(12) United States Patent
Zeng et al.

(10) Patent No.: US 11,401,622 B2
(45) Date of Patent: Aug. 2, 2022

(54) COMPOSITE ARRAY ELECTRODE, PREPARATION METHOD THEREOF AND USE THEREOF

(71) Applicant: SHENZHEN INSTITUTES OF ADVANCED TECHNOLOGY, Guangdong (CN)

(72) Inventors: Qi Zeng, Guangdong (CN); Tianzhun Wu, Guangdong (CN)

(73) Assignee: SHENZHEN INSTITUTES OF ADVANCED TECHNOLOGY, Guangdong (CN)

( * ) Notice: Subject to any disclaimer, the term of this patent is extended or adjusted under 35 U.S.C. 154(b) by 212 days.

(21) Appl. No.: 16/618,052

(22) PCT Filed: Dec. 15, 2018

(86) PCT No.: PCT/CN2018/121354
§ 371 (c)(1),
(2) Date: Nov. 27, 2019

(87) PCT Pub. No.: WO2020/118732
PCT Pub. Date: Jun. 18, 2020

(65) Prior Publication Data
US 2021/0102304 A1 Apr. 8, 2021

(51) Int. Cl.
*A61B 5/268* (2021.01)
*C25D 7/12* (2006.01)
(Continued)

(52) U.S. Cl.
CPC .............. *C25D 7/12* (2013.01); *A61B 5/1468* (2013.01); *A61B 5/268* (2021.01); *B08B 3/08* (2013.01);
(Continued)

(58) Field of Classification Search
CPC .......... A61B 2562/028; A61B 2562/04; A61B 2562/046; A61B 2562/125;
(Continued)

(56) References Cited

U.S. PATENT DOCUMENTS

| 7,435,488 B2* | 10/2008 | Tomita ................... B82Y 10/00 |
| | | 427/129 |
| 2010/0233226 A1* | 9/2010 | Ferain ...................... A61P 25/06 |
| | | 424/422 |

(Continued)

FOREIGN PATENT DOCUMENTS

| CN | 101214149 A | 7/2008 |
| CN | 108744268 A | 11/2018 |
| KR | 20150095964 A | 8/2015 |

OTHER PUBLICATIONS

International Search Report and Written Opinion For PCT/CN2018/121354 dated Dec. 15, 2018, 4 pages.

*Primary Examiner* — George Manuel
(74) *Attorney, Agent, or Firm* — Dinsmore & Shohl LLP

(57) ABSTRACT

Provided are composite array electrode, preparation method thereof and use thereof. The composite array electrode comprises a microelectrode array substrate, and a modification layer formed on a surface of a microelectrode of the microelectrode array substrate, wherein the modification layer comprises a plurality of electrically conductive layers arranged at intervals on the surface of the microelectrode, an insulating layer arranged on the surface of the microelectrode except the electrically conductive layers, and wherein material for the electrically conductive layers comprises one or more of nano platinum, nano iridium, conductive polymer and carbon nanotubes. The composite array electrode effectively eliminates the influence of edge effect such that the electric field distributes uniformly on the microelectrode surface of the composite array electrode, significantly (Continued)

improving electrochemical performance and detection capability of the electrode.

9 Claims, 4 Drawing Sheets

(51) Int. Cl.
    *A61B 5/1468*     (2006.01)
    *B08B 3/08*     (2006.01)
    *B08B 7/02*     (2006.01)
    *C25D 5/02*     (2006.01)
    *C25D 5/34*     (2006.01)
    *G01N 27/327*     (2006.01)
    *A61N 1/05*     (2006.01)

(52) U.S. Cl.
    CPC ............... B08B 7/028 (2013.01); C25D 5/02 (2013.01); C25D 5/34 (2013.01); G01N 27/3278 (2013.01); *A61B 2562/028* (2013.01); *A61B 2562/04* (2013.01); *A61B 2562/046* (2013.01); *A61B 2562/125* (2013.01); *A61N 1/0551* (2013.01)

(58) Field of Classification Search
    CPC ... A61B 5/14532; A61B 5/1468; A61B 5/268; A61N 1/05; A61N 1/0551; B08B 3/08; B08B 7/028; C25D 13/22; C25D 3/50; C25D 5/02; C25D 5/34; C25D 7/12; C25D 9/08; G01N 27/3278; H01L 23/522
    See application file for complete search history.

(56) References Cited

U.S. PATENT DOCUMENTS

| | | | |
|---|---|---|---|
| 2011/0053794 A1* | 3/2011 | Zhang | B01J 19/0046 506/9 |
| 2016/0195488 A1* | 7/2016 | Ensor | G01N 27/227 422/69 |

* cited by examiner

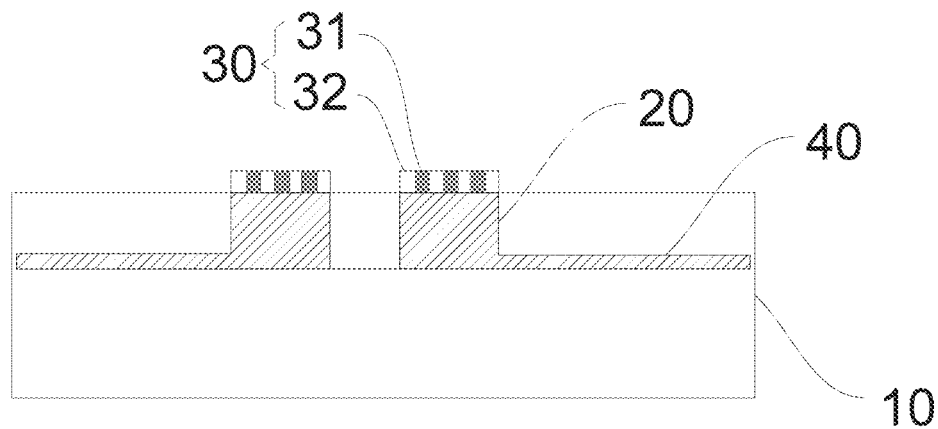

FIG. 2

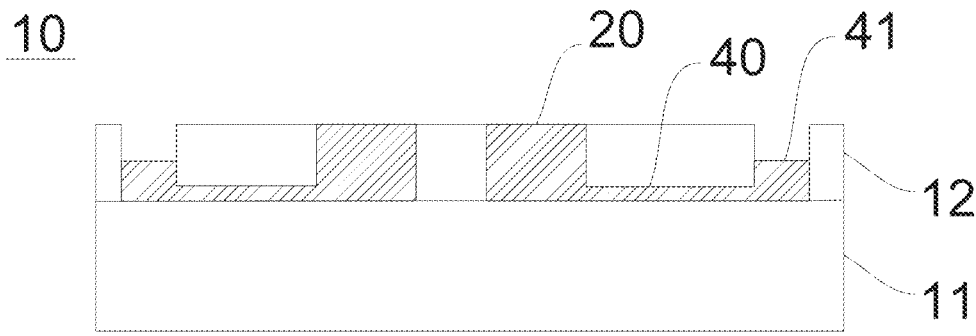

FIG. 3

| providing a microelectrode array substrate, the microelectrode of the microelectrode array substrate being provided with an insulating layer on the surface thereof; etching the insulating layer to form a plurality of holes spaced apart and penetrating the insulating layer; | S10 |

↓

| depositing an electrically conductive material in the holes to form an electrically conductive layer on the surface of the microelectrode by electrodeposition process, the electrically conductive material comprising one or more of nano platinum, nano iridium, electrically conductive polymer and carbon nanotubes. | S20 |

FIG. 4

COMPOSITE ARRAY ELECTRODE, PREPARATION METHOD THEREOF AND USE THEREOF

FIELD OF THE INVENTION

The invention relates to materials for electrocatalysis, in particular to composite array electrode, preparation method thereof and use thereof.

BACKGROUND OF THE INVENTION

As one of the most important implantable micro devices, the neural electrode is used for stimulating nervous tissue or record electroneurographic signal, and is widely applied in life science fields such as neurophysiology and brain science research. Currently, neural electrodes are developing towards integrated and miniaturized microelectrode arrays. However, the reduction of electrode size may lead to problems such as the increase of electrode impedance and decrease of capacitance, which greatly affects the electrochemical properties of the electrode and restricts the application of the electrode in fields such as physiological parameter detection and life science.

In the prior art, surface modification is usually used for improving the electrochemical properties of electrodes; however, since the electric field distribution is not even between the electrode edge and the central part, during the electroplating process, the higher density of electric field distribution at the electrode edge may lead to quick electrodeposition and edge effect, thus resulting in the uneven plating thickness of the edge and the central part and poor electrochemical properties; besides, the smaller the electrode is, the more severe the edge effect is. Currently, there are several mature processing technologies, including the reduction of edge effect of copper, which forms a layer of metallic seed layer on base surface and performs annealing treatment before electroplating (Patent 102790009A, 2012), or changing electroplating liquid ingredients and design of a special spraying mechanism in electroplating devices to evenly distribute the concentration of electroplating liquid for improving evenness (U.S. patent Ser. No. 07/459,892, 1990; Patent 206109565U, 2017); or design of an electroplating baffle to block the electric field line bypassing the baffle edge to eliminate edge effect (Patent 200999265Y, 2008). Although these methods can eliminate edge effect to a certain extent, they are mostly used in large components, and are not applicable to micro-nano electrode and are not easy to operate. Therefore, for neural electrodes, especially the surface modification of micro-nano size electrodes, it is difficult to solve the edge effect well.

SUMMARY OF THE INVENTION

In view of this, the present invention provides composite array electrode, preparation method thereof and use thereof. The composite array electrode effectively eliminates the influence of edge effect such that the electric field distributes uniformly on the microelectrode surface of the composite array electrode, significantly improving electrochemical performance and detection capability of the electrode.

In a first aspect, the present invention provides a composite array electrode comprising: a microelectrode array substrate and a modification layer formed on a surface of a microelectrode of the microelectrode array substrate, wherein the modification layer comprises a plurality of electrically conductive layers arranged at intervals on the surface of the microelectrode, an insulating layer arranged on the surface of the microelectrode except the electrically conductive layers, and wherein material for the electrically conductive layers comprises one or more of nano platinum, nano iridium, electrically conductive polymer and carbon nanotubes.

Alternatively, the electrically conductive polymer comprises one or more of polyaniline, polypyrrole and polythiophene. Alternatively, the electrically conductive polymer comprises one or more of a polyaniline derivative, a polypyrrole derivative and a polythiophene derivative.

Alternatively, each of the electrically conductive layers has a lateral dimension of 6 to 60 μm.

Alternatively, a plurality of the electrically conductive layers are arranged on the surface of the microelectrode in an array.

Alternatively, a total area of the electrically conductive layers is from 50% to 80% of the surface of the microelectrode.

Alternatively, the electrically conductive layers have a thickness of 0.02 to 10 μm.

Alternatively, an allowable difference between the thickness of the edge of the electrically conductive layer and the thickness of the central region of the conductive layer is less than 0.1 μm.

Alternatively, the microelectrode array substrate comprises a flexible electrode substrate or a hard electrode substrate.

The composite arrayed electrode provided in the first aspect of the present invention disperses the unevenly distributed electric field of microelectrodes through arrayed arrangement of a plurality of high-performance electrically conductive layers on the surface of microelectrode such that the electric field evenly applies to the electrically conductive layer; in the meanwhile, the 3D nano structure based on electrically conductive layer provides huge surface area, which greatly improves electrochemical property of electrode, so that the entire composite arrayed electrode has low impedance, high charge storage capability and charge injection capability, good mechanical stability and electrochemical stability. Such composite arrayed electrode is featured by wide detection range and good detection linearity and will be widely applied in non-enzymatic glucose detection and the life science fields such as neurophysiology and brain science research.

In a second aspect, the present invention further provides a method for preparing a composite array electrode, comprising:

providing a microelectrode array substrate, the microelectrode of the microelectrode array substrate being provided with an insulating layer on the surface thereof; etching the insulating layer to form a plurality of holes spaced apart and penetrating the insulating layer;

depositing an electrically conductive material in the holes to form an electrically conductive layer on the surface of the microelectrode by electrodeposition process, the electrically conductive material comprising one or more of nano platinum, nano iridium, electrically conductive polymer and carbon nanotubes.

Alternatively, after the step of etching the insulating layer and before performing the electrodeposition process, the method further comprises performing surface pretreatment on the etched microelectrode array substrate, and the step of performing surface pretreatment comprises:

cleaning ultrasonically the etched microelectrode array substrate in an acetone or ethanol solution for 20 to 60 minutes, followed by washing with deionized water and placing in a sulfuric acid solution for electrochemical cyclic voltammetry scanning under a voltage of −0.25V~1.2V, at a scanning rate of 50~200 mV/s, for a scanning time of 25~60 min, until a coincident CV curve is obtained.

Alternatively, where the electrically conductive material is nano platinum, the electrodeposition process comprises:
preparing a platinum salt solution;
placing the surface-pretreated microelectrode array substrate in the platinum salt solution and performing electrodepositing such that an electrically conductive material is deposited in the holes to form an electrically conductive layer on the surface of the microelectrode,
wherein the platinum salt in the platinum salt solution comprises one or more of platinum chloride, ammonium hexachloroplatinate, potassium hexachloroplatinate, sodium hexachloroplatinate, chloroplatinic acid, platinum nitrate, platinum sulfate, potassium tetrachloroplatinate and ammonium tetrachloroplatinate, and the platinum salt solution has a pH of 6.5 to 7.5.

Alternatively, the platinum salt solution further comprises a buffering agent, which comprises one or more of a phosphate buffer, a Tris-HCl buffer and a borate buffer.

Alternatively, the holes have a cross-sectional shape of one or more of circle, triangle, quadrangle and polygon, and the holes have a lateral dimension of 6 to 60 μm.

The method for preparing a composite array electrode provided by the second aspect of the present invention effectively eliminates the influence of the edge effect. A plurality of spaced electrically conductive layers are arranged on the surface of the microelectrode of the microelectrode array substrate. On one hand, the electrically conductive layer improves electrochemical performance of the microelectrode. On the other hand, the electrically conductive layer disperses the unevenly distributed electric field of microelectrodes, so that the resultant composite array electrode has a stable and even distribution of the electric field. The method for preparing composite array electrode has the advantages of simple and easy operation, low cost and easy to implement.

In a third aspect, the present invention provides use of the composite array electrode described in the first aspect of the invention or the composite array electrode prepared by the preparation method of the second aspect of the invention in biochemical analysis or life science field, for example, the application of implantable nerve electrode devices, glucose detection and others. The composite array electrode of the present invention has excellent and stable electrochemical performance, and superior detection capability, and thus the composite array electrode is applicable to various biochemical analysis detection or life science fields.

Alternatively, the application of the composite array electrode includes, but is not limited to, sensing or stimulation analysis detection.

The advantages of the invention will be set forth in the description.

BRIEF DESCRIPTION OF THE DRAWINGS

To make the objectives, technical solutions, and advantages of the present invention more comprehensible, the following further describes the embodiments of the present invention in detail with reference to the accompanying drawings.

FIG. 2 is a cross-sectional view of composite array electrode 100 in accordance with the present invention.

FIG. 3 is a cross-sectional view of microelectrode array in accordance with the present invention.

FIG. 4 is a flowchart of a method for preparing composite array electrode in accordance with the present invention.

FIG. 5(a) shows the entirety of two electrodes. FIG. 5(b) shows part of two electrodes. FIG. 5(c) shows an unmodified microelectrode for an existing microelectrode array. FIG. 5(d) shows a platinum modification layer containing microelectrode for an existing microelectrode array. FIG. 5(e) shows electric field distribution of the platinum modification layer containing microelectrode for an existing microelectrode array. FIG. 5(f) shows an unmodified microelectrode for the composite array electrode. FIG. 5(g) shows the nano platinum electrically conductive layer containing microelectrode for the modified composite array electrode. FIG. 5(h) shows electric field distribution of the nano platinum electrically conductive layer containing microelectrode for the modified composite array electrode.

FIG. 6(a) is an electron micrograph of a platinum modification layer of a microelectrode for the existing microelectrode array. FIG. 6(b) shows an electron micrograph and a partial enlarged view of the nano platinum electrically conductive layer modified microelectrode for the composite array electrode. FIG. 6(c) is an electron micrograph of single nano platinum electrically conductive layer of the composite array electrode. FIG. 6(d) shows partial enlarged view of the nano platinum electrically conductive layer modified microelectrode for the composite array electrode.

DETAILED DESCRIPTION OF THE INVENTION

Some preferred embodiments of the present invention will be described below. Those skilled in the art should understand that the modifications or equivalent substitutions of the embodiments are not intended to be excluded from the scope of the invention.

The present invention will be further described below in various embodiments. The embodiments of the present invention are not limited to the following specific embodiments. Any variation within the technical scope disclosed in the present invention shall fall within the protection scope of the present invention.

Unless otherwise stated, the raw materials and other chemical reagents used in the present invention are all purchased from the market.

Figure 1:
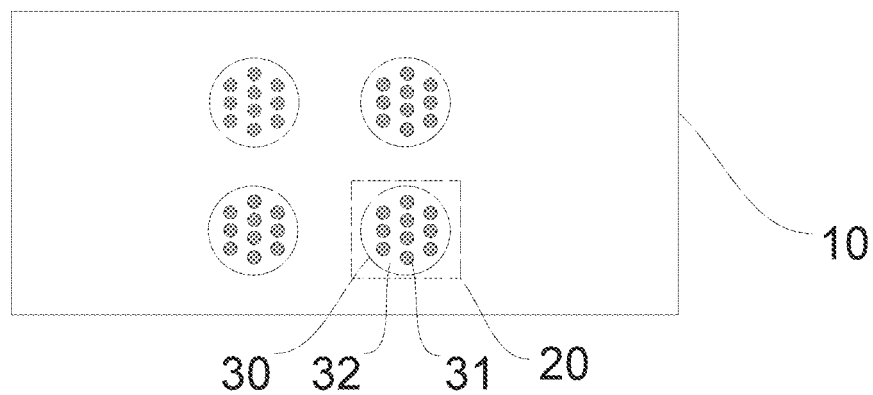
FIG. 1 shows the structure of composite array electrode 100 in accordance with the present invention.

Referring to FIG. 1 and FIG. 2, an embodiment of the present invention provides a composite array electrode 100, comprising a microelectrode array substrate 10, and a modification layer 30 formed on a surface of a microelectrode 20 of the microelectrode array substrate 10, wherein the modification layer 30 comprises a plurality of electrically conductive layers 31 arranged at intervals on the surface of the microelectrode 20, an insulating layer 32 arranged on the surface of the microelectrode 20 except the electrically conductive layers 31, and wherein material for the electrically conductive layers 31 comprises one or more of nano platinum, nano iridium, conductive polymer and carbon nanotubes.

In one embodiment, the microelectrode array substrate 10 is provided with a plurality of microelectrodes 20, which may be, but not limited to, arranged on the microelectrode array substrate 10 in an array. Alternatively, each of the microelectrodes is further connected with a lead 40 arranged on the microelectrode array substrate 10. In one embodiment of the present invention, the microelectrode array substrate 10 comprises a flexible electrode substrate or a hard electrode substrate. Where the microelectrode array substrate comprises a substrate layer and a metal layer, the substrate layer of the microelectrode array substrate in the form of a flexible electrode substrate is prepared from a flexible material, and the metal layer is advantageously bendable. The microelectrode array substrate 10 may be a microelectrode array of various structures; for example, the microelectrode array substrate 10 comprises an insulating base 11 on which a plurality of sets of microelectrodes 20 are arranged, each of the microelectrodes 20 is led out by lead 40 covered with a second insulating layer 12, which is exposed from the microelectrode 20 and the pad 41 of the lead 40, see FIG. 3.

Alternatively, the microelectrode 20 on the microelectrode array substrate 10 has a lateral dimension of 150 to 300 µm. Further, alternatively, the microelectrode 20 has a lateral dimension of 150 to 250 µm. For example, the microelectrode 20 has a lateral dimension of 150 µm, or 180 µm, or 200 µm, or 230 µm, or 250 µm, etc. The lateral dimension of the microelectrode can be considered to be the maximum distance between any two points on the edge of the cross-sectional shape of the microelectrode in the horizontal direction. For example, where the cross-sectional shape of the microelectrode is circular, the lateral dimension of the microelectrode is the diameter of the circular. Where the cross-sectional shape of the microelectrode is rectangular, the lateral dimension of the microelectrode is length of the long side of the rectangle.

In this embodiment, the insulating layer may be, but not limited to, made of an insulating polymer material. Alternatively, material for the insulating layer may be, but not limited to, plastic or rubber. Alternatively, material for the insulating layer may include, but is not limited to, one or more of polyimide, polydimethylsiloxane, polychloro-p-xylene, silica gel, polyurethane and epoxy resin.

Alternatively, in the modification layer, the cross-sectional shape of the electrically conductive layers includes one or more of circle, triangle, quadrangle and polygon. Preferably, the cross-sectional shape of the electrically conductive layers includes a circular shape. In this embodiment, a plurality of the electrically conductive layers are arranged on the surface of the microelectrode in an array. For example, two adjacent electrically conductive layers are spaced equally. The electrically conductive layers may also be regularly arranged on the surface of the microelectrode. The cross-sectional shape of the microelectrode may be, but not limited to, a circular shape. Where the cross-sectional shape of the microelectrode is circular, a plurality of the electrically conductive layers may be regularly arranged around the center of the circular cross-section of the microelectrode. The spaced electrically conductive layers can effectively improve the electric field distribution of the microelectrode, dispersing the uneven electric field distribution of the microelectrode such that the electric field distribution finally applied to the electrically conductive layer is relatively uniform.

Alternatively, each of the electrically conductive layers has a lateral dimension of 6 to 60 µm. Further, alternatively, each of the electrically conductive layers has a lateral dimension of 15 to 35 µm. For example, each of the electrically conductive layers has a lateral dimension of 10 µm, or 15 µm, or 20 µm, or 25 µm, or 30 µm, or 35 µm, or 45 µm, or 50 µm, etc.

Alternatively, a total area of the electrically conductive layers is from 50% to 80% of the surface of the microelectrode. Further, alternatively, a total area of the electrically conductive layers is from 50% to 70% of the surface of the microelectrode. For example, a total area of the electrically conductive layers is 50%, or 55%, or 60%, or 65%, or 70%, or 80% of the surface of the microelectrode. Total area of the electrically conductive layers in the above preferred range can greatly improve electrochemical performance of the entire microelectrode.

In this embodiment, the surface of the microelectrode is a side surface away from the insulating base of the microelectrode array. Where the microelectrode is a protruding cylindrical electrode, the modification layer covers the entire microelectrode, and the modification layer on the circular top surface of the microelectrode may include a plurality of electrically conductive layers arranged at intervals, while the modification layer on the side of the cylindrical microelectrode may not contain an electrically conductive layer, and a region outside the electrically conductive layer on the surface of the microelectrode is an insulating layer. Alternatively, a plurality of spaced-apart electrically conductive layers are arranged on the entire circular top surface and side of the cylindrical microelectrode, and a region outside the electrically conductive layer on the surface of the microelectrode is an insulating layer.

In this embodiment, the electrically conductive layer has a thickness of 0.02 to 10 µm. Further, alternatively, the electrically conductive layer has a thickness of 0.05 to 5 µm. For example, the electrically conductive layer has a thickness of 0.02 µm, 0.2 µm, or 0.3 µm, or 0.5 µm, or 0.8 µm, or 1.0 µm, or 1.5 µm, or 3.0 µm, or 4.0 µm, or 5.0 µm, or 10 µm, etc. Each of the electrically conductive layers of the present invention has a consistent thickness. Alternatively, an allowable difference between the thickness of the edge of the electrically conductive layer and the thickness of the central region of the conductive layer is less than 0.1 µm. Further, alternatively, an allowable difference between the thickness of the edge of the electrically conductive layer and the thickness of the central region of the conductive layer is less than 0.08 µm. The consistent thickness of the entire electrically conductive layer can eliminate the influence of the edge effect, making the electric field distribution of the electrically conductive layer more uniform and electrochemical performance of the surface of the electrically conductive layer more balanced and stable. As that microelectrode on the composite array electrode of the invention has more excellent and stable electrochemical performance, a more subtle signal can be obtained with a high accuracy. Therefore, the composite array electrode can be used in fields where the requirements for the electrodes are very demanding, for example, an implantable nerve electrode or the like. In this embodiment, thickness of the electrically conductive layer is greater than or equal to thickness of the insulating layer on the surface of the microelectrode.

Alternatively, material for the electrically conductive layer 31 of the present invention includes, but is not limited to, one or more of nano platinum, nano iridium, electrically conductive polymer and carbon nanotubes. For example, material for the electrically conductive layer may be nano platinum; alternatively, material for the electrically conductive layer may be nano iridium; alternatively, material for the electrically conductive layer may be electrically conductive polymer; alternatively, material for the electrically conductive layer may be carbon nanotubes; alternatively, material for the electrically conductive layer may be a composite nano material of nano platinum and nano iridium. The nano materials, such as nano platinum, nano iridium, electrically conductive polymer and carbon nanotubes, have great surface area and stable performance, and can improve electrochemical performance of the entire microelectrode.

The composite arrayed electrode provided in the first aspect of the present invention disperses the unevenly distributed electric field of microelectrodes through arrayed arrangement of a plurality of high-performance electrically conductive layers on the surface of microelectrode such that the electric field evenly applies to the electrically conductive layer; in the meanwhile, the 3D nano structure based on electrically conductive layer provides huge surface area, which greatly improves electrochemical property of electrode, so that the entire composite arrayed electrode has low impedance, high charge storage capability and charge injection capability, good mechanical stability and electrochemical stability. Such composite arrayed electrode is featured by wide detection range and good detection linearity and will be widely applied in non-enzymatic glucose detection and the life science fields such as neurophysiology and brain science research.

Referring to FIG. 4, another embodiment of the present invention further provides a method for preparing a composite array electrode, comprising:

S10, providing a microelectrode array substrate, the microelectrode of the microelectrode array substrate being provided with an insulating layer on the surface thereof; etching the insulating layer to form a plurality of holes spaced apart and penetrating the insulating layer;

S20, depositing an electrically conductive material in the holes to form an electrically conductive layer on the surface of the microelectrode by electrodeposition process, the electrically conductive material comprising one or more of nano platinum, nano iridium, electrically conductive polymer and carbon nanotubes.

Specifically, at step S10, the microelectrode array substrate is provided with a plurality of microelectrodes, which may be, but not limited to, arranged on the microelectrode array substrate in an array. The insulating layer on the surface of the microelectrode of the microelectrode array substrate may be formed by coating or spraying an insulating material on the microelectrode array substrate.

Alternatively, the insulating layer is etched by applying photomask through the step of coating, exposing, developing, etching, stripping such that a plurality of holes spaced apart and penetrating the insulating layer are formed on the insulating layer, and the holes expose the surface of the microelectrode. Alternatively, at step S10, plasma etching process or laser machining process may be performed to etch the insulating layer.

Alternatively, after the step of etching the insulating layer and before performing the electrodeposition process, the method further comprises performing surface pretreatment on the etched microelectrode array substrate, and the step of performing surface pretreatment comprises:

cleaning ultrasonically the etched microelectrode array substrate in an acetone or ethanol solution for 20 to 60 minutes, followed by washing with deionized water and placing in a sulfuric acid solution for electrochemical cyclic voltammetry scanning under a voltage of −0.25V~1.2V, at a scanning rate of 50~200 mV/s, for a scanning time of 25~60 min, until a coincident CV curve is obtained. Alternatively, the concentration of the sulfuric acid is in a range of 0.03 to 0.8M. For example, the concentration of the sulfuric acid is 0.03 M, or 0.05 M, or 0.08 M, or 0.3 M, or 0.8 M, etc. In this embodiment, the microelectrode array substrate is subjected to a surface pretreatment so as to bind to the nanomaterial to be deposited more firmly.

Alternatively, the holes have a cross-sectional shape of one or more of circle, triangle, quadrangle and polygon. The polygon may be a pentagon or a hexagon, etc. Alternatively, the holes have a lateral dimension of 10 to 50 μm.

Specifically, at step S20, where the electrically conductive material is nano platinum, the electrodeposition process comprises:

preparing a platinum salt solution;

placing the surface-pretreated microelectrode array substrate in the platinum salt solution and performing electrodepositing such that an electrically conductive material is deposited in the holes to form an electrically conductive layer on the surface of the microelectrode, wherein the platinum salt in the platinum salt solution comprises one or more of platinum chloride, ammonium hexachloroplatinate, potassium hexachloroplatinate, sodium hexachloroplatinate, chloroplatinic acid, platinum nitrate, platinum sulfate, potassium tetrachloroplatinate and ammonium tetrachloroplatinate, and the platinum salt solution has a pH of 6.5 to 7.5.

Alternatively, the step of placing the surface-pretreated microelectrode array substrate in the platinum salt solution and performing electrodepositing further comprises: allowing the surface-pretreated microelectrode array substrate standing in the platinum salt solution for 5~20 min in advance.

In this embodiment, where the platinum salt in the platinum salt solution comprises two of platinum chloride, ammonium hexachloroplatinate, potassium hexachloroplatinate, sodium hexachloroplatinate, chloroplatinic acid, platinum nitrate, platinum sulfate, potassium tetrachloroplatinate and ammonium tetrachloroplatinate, the concentrations of the two platinum salt Alternatively, the platinum salt solution further comprises a buffering agent, which comprises one or more of a phosphate buffer, a Tris-HCl buffer and a borate buffer. Further, alternatively, in the platinum salt solution, the concentration of the buffer is in a range of 0.1 to 100 mM. For example, the platinum salt solution contains a phosphate buffer having a hydrogen phosphate ion concentration of 0.01 mM to 1 mM and a dihydrogen phosphate ion concentration of 0.5 mM to 50 mM.

Alternatively, the platinum salt solution has a platinum ion concentration of 5 mM to 50 mM. Further, alternatively, the platinum salt solution has a platinum ion concentration of 10 mM to 30 mM. For example, the platinum salt solution has a platinum ion concentration of 5 mM, or 10 mM, or 15 mM, or 20 mM, or 30 mM, or 40 mM, or 50 mM, etc.

Alternatively, the electrically conductive material may be electrodeposited by a constant potential deposition process at a potential of −0.5V to −0.75V or a constant current deposition process at a current of −0.25 μA to −5 μA. Alternatively, the electrodeposition process is performed for 20 to 60 min. The deposition time of the electrodeposition process is related to the magnitude of the potential or current and the thickness of the electrically conductive layer. Alternatively, the electrically conductive layer has a thickness of 0.02 to 10 μm. In this embodiment, the resultant electrically conductive layer has a consistent thickness. Alternatively, an allowable difference between the thickness of the edge of the electrically conductive layer and the thickness of the central region of the conductive layer is less than 0.1 μm.

Alternatively, where the electrically conductive material is nano iridium, the electrodeposition process comprises:

preparing an iridium salt solution;

placing the surface-pretreated microelectrode array substrate in the iridium salt solution and performing electrodepositing such that an electrically conductive material is deposited in the holes to form the electrically conductive layer on the surface of the microelectrode, wherein the iridium salt in the iridium salt solution comprises one or more of iridium chloride, chloroiridic acid, sodium hexachloroiridate and potassium hexachloroiridate, and the iridium salt solution has a pH of 6.5 to 7.5.

Alternatively, where the electrically conductive material is an electrically conductive polymer, the electrically conductive polymer in the solution comprises one or more of polyaniline, polypyrrole and polythiophene. Alternatively, the electrically conductive polymer comprises one or more of a polyaniline derivative, a polypyrrole derivative and a polythiophene derivative.

Alternatively, where the electrically conductive material is carbon nanotubes, the carbon nanotubes are single-walled or multi-walled carbon nanotubes, and the carbon nanotubes have a pore size of 30 to 45 μm. The method for preparing a composite array electrode provided by the present invention effectively eliminates the influence of the edge effect. A plurality of spaced electrically conductive layers are arranged on the surface of the microelectrode of the microelectrode array substrate. On one hand, the electrically conductive layer improves electrochemical performance of the microelectrode. On the other hand, the electrically conductive layer disperses the unevenly distributed electric field of microelectrodes, so that the resultant composite array electrode has a stable and even distribution of the electric field. The method for preparing composite array electrode has the advantages of simple and easy operation, low cost and easy to implement.

Example 1

A method for preparing a composite array electrode comprises the following steps.

A microelectrode array substrate was provided. The microelectrode array substrate was provided with an insulating layer on the surface of the microelectrode array. The microelectrode on the microelectrode array substrate had a lateral dimension of about 200 μm. A porous mask was designed to comprise a plurality of holes arranged in an array, each of the holes having a diameter of about 10 μm. A plurality of the holes in an array were correspondingly etched on the insulating layer on the surface of the microelectrode by a photo etching machine and the porous mask. The insulating layer was made of polyimide.

The etched microelectrode array substrate was ultrasonically cleaned in acetone solution for 30 min, and then washed with deionized water and placed in 0.05 M sulfuric acid solution for electrochemical cyclic voltammetry scanning under a voltage of −0.25V~1.2V, at a scanning rate of 100~200 mV/s, for a scanning time of 30 min, until a coincident CV curve was obtained. The substrate was then washed with deionized water to produce a surface-pretreated microelectrode array substrate for later use.

Two platinum salts of ammonium hexachloroplatinate and sodium chloroplatinate in a volume ratio of 1:4 were mixed to obtain a concentration of the ammonium hexachloroplatinate of 30 mM and a concentration of sodium chloroplatinate of 5 mM, and phosphate was added to produce a platinum salt solution having a pH of 7.0. The surface-pretreated microelectrode array substrate was placed in a platinum salt solution for 10 min, and then platinum was electrodeposited by a constant potential deposition process at a potential of −0.65 V for 10 min to form a nano platinum electrically conductive layer in the hole. After the deposition, the substrate was washed with deionized water, and a composite array electrode was obtained. The nano platinum electrically conductive layer had a thickness of 5 μm.

Figure 5:
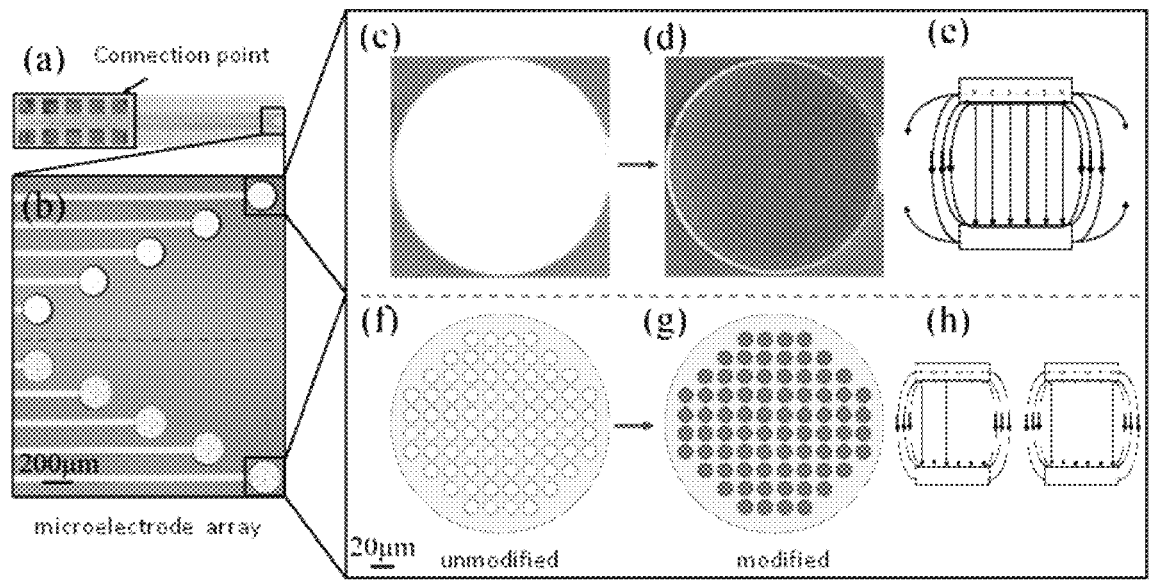
FIG. 5 shows comparison of an existing microelectrode array and a composite array electrode in accordance with the present invention.
Figure 6:
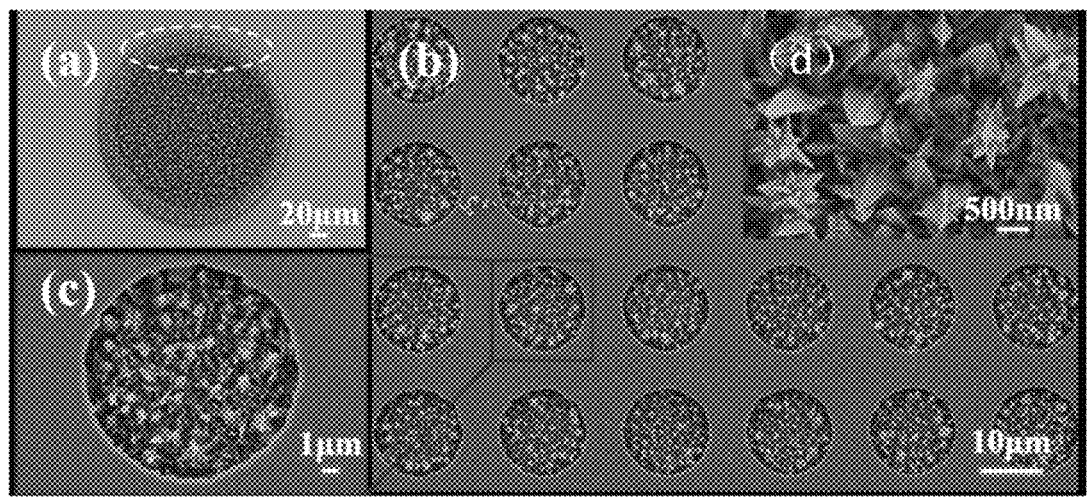
FIG. 6 shows electron micrographs of a microelectrode for an existing microelectrode array and microelectrode for the composite array electrode according to an embodiment of the present invention.

Comparing the resultant composite array electrode with the existing microelectrode array, as shown in FIG. 5, for the composite array electrode, the electric field distributed evenly in a single electrically conductive layer (FIG. 5(*g*)); for the existing microelectrode array, the electric field distribution was unevenly distributed in the edge and the central region of the microelectrode, although the microelectrode array was provided with platinum modification layer (FIG. 5(*d*)), as shown in FIG. 5 (*e*) and FIG. 5 (*h*). The composite array electrode and the existing microelectrode array were further subjected to analysis by scanning electron microscopy, see FIG. 6. The results showed that thickness of the edge was different from that of the central region of the existing microelectrode array microelectrode, and the edge region was significantly denser than the central region. On the electrically conductive layer of the microelectrode of the composite array electrode, nano platinum distributed evenly. The edge and the central region of the electrically conductive layer had a similar microstructure, and all the electrically conductive layers tend to be uniform.

Example 2

A method for preparing a composite array electrode comprises the following steps.

A microelectrode array substrate was provided. An insulating layer of polydimethylsiloxane was coated on the surface of the microelectrode of the microelectrode array substrate. The microelectrode of the microelectrode array substrate had a lateral dimension of about 200 μm. A porous mask was designed to comprise a plurality of holes arranged at intervals, each of the holes having a diameter of about 10 μm. A plurality of the holes spaced apart were correspondingly etched on the insulating layer on the surface of the microelectrode by a photo etching machine and the porous mask.

The etched microelectrode array substrate was ultrasonically cleaned in acetone solution for 30 min, and then washed with deionized water and placed in 0.05 M sulfuric acid solution for electrochemical cyclic voltammetry scanning under a voltage of −0.25V~1.2V, at a scanning rate of 100~200 mV/s, for a scanning time of 30 min, until a coincident CV curve was obtained. The substrate was then washed with deionized water to produce a surface-pretreated microelectrode array substrate for later use.

To a 30 mM iridium chloride solution was added 20 mM of phosphate to prepare an iridium salt solution having a pH of 7.0. The surface-pretreated microelectrode array substrate was placed in an iridium salt solution for 10 min, and then platinum was electrodeposited by a constant potential deposition process at a potential of −0.80 V for 15 min to form a nano iridium electrically conductive layer in the hole. After the deposition, the substrate was washed with deionized water, and a composite array electrode was obtained. The nano iridium electrically conductive layer had a thickness of 8 μm.

Example 3

A method for preparing a composite array electrode comprises the following steps.

A microelectrode array substrate was provided. An insulating layer of polychloro-p-xylene was coated on the surface of the microelectrode of the microelectrode array substrate. The microelectrode of the microelectrode array substrate had a lateral dimension of about 200 μm. The microelectrode of the microelectrode array substrate had a lateral dimension of about 200 μm. A plurality of the holes in an array were correspondingly etched on the insulating layer on the surface of the microelectrode by a plasma etching process. The diameter of the holes was about 10 μm.

The etched microelectrode array substrate was ultrasonically cleaned in acetone solution for 35 min, and then washed with deionized water and placed in 0.05 M sulfuric acid solution for electrochemical cyclic voltammetry scanning under a voltage of −0.25V~1.2V, at a scanning rate of 100~200 mV/s, for a scanning time of 30 min, until a coincident CV curve was obtained. The substrate was then washed with deionized water to produce a surface-pretreated microelectrode array substrate for later use.

A phosphate buffer was added to a 30 mM polyaniline solution to adjust the pH to 7.0. The surface-pretreated microelectrode array substrate was placed in a polyaniline solution for 10 min, and then platinum was electrodeposited by a constant potential deposition process at a potential of −0.80 V for 20 min to form a polyaniline electrically conductive layer in the hole. After the deposition, the substrate was washed with deionized water, and a composite array electrode was obtained. The polyaniline electrically conductive layer had a thickness of 10 μm.

Example 4

A method for preparing a composite array electrode comprises the following steps.

A microelectrode array substrate was provided. An insulating layer of polydimethylsiloxane was coated on the surface of the microelectrode of the microelectrode array substrate. The microelectrode of the microelectrode array substrate had a lateral dimension of about 250 μm. A porous mask was designed to comprise a plurality of holes arranged at intervals, each of the holes having a diameter of about 8 μm. A plurality of the holes spaced apart were correspondingly etched on the insulating layer on the surface of the microelectrode by a photo etching machine and the porous mask.

The etched microelectrode array substrate was ultrasonically cleaned in an ethanol solution for 30 min, and then washed with deionized water and placed in a 0.05 M sulfuric acid solution for electrochemical cyclic voltammetry scanning under a voltage of −0.25V~1.2V, at a scanning rate of 100~200 mV/s, for a scanning time of 30 min, until a coincident CV curve was obtained. The substrate was then washed with deionized water to produce a surface-pretreated microelectrode array substrate for later use.

A 0.3 mg/mL carbon nanotubes solution was prepared, adjusting the pH to 7.0. The pore size of the carbon nanotubes was 40 μm. The surface-pretreated microelectrode array substrate was placed in the carbon nanotubes solution for 15 min, and then platinum was electrodeposited by a constant current deposition process at a current of −0.25 μA for 20 min to form a nano carbon nanotubes electrically conductive layer in the hole. After the deposition, the substrate was washed with deionized water, and a composite array electrode was obtained. The carbon nanotubes electrically conductive layer had a thickness of 8 μm.

Effectiveness Example 1—Evaluation of Electrochemical Performance of the Composite Array Electrode Prepared by the Present Invention The composite array electrode (C) containing the nano platinum electrically conductive layer, the microelectrode array (B) containing the nano platinum modification layer, and the unmodified microelectrode array (A) were placed in PBS solution for cyclic voltammetry (CV) test under the same condition. The microelectrode array (B) containing the nano platinum modification layer referred to a microelectrode array modified with a nano platinum layer on the entire surface of the microelectrode thereof.

Figure 7:
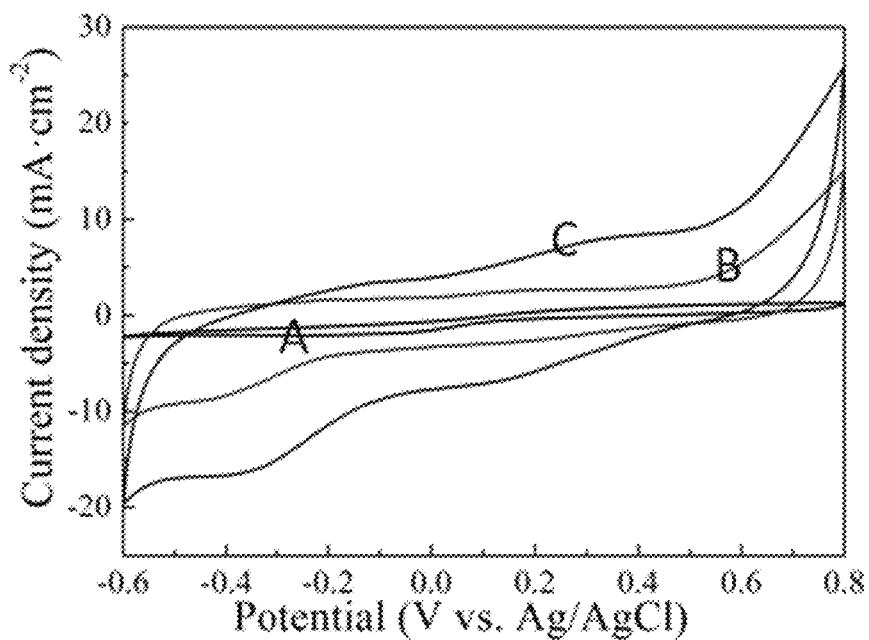
FIG. 7 shows cyclic voltammetry characteristics of different electrodes of the present invention. The electrodes are: an unmodified microelectrode array A, a microelectrode array B containing a platinum modification layer, and a composite array electrode C containing a nano platinum electrically conductive layer.

The results showed that, referring to FIG. 7, the CV area for the composite array electrode (C) prepared by the present invention was significantly increased compared with the microelectrode array (B) containing the nano platinum modification layer, while the charge storage capacity for the composite array electrode (C) was about 100 times larger than the microelectrode array (B).

Figure 8:
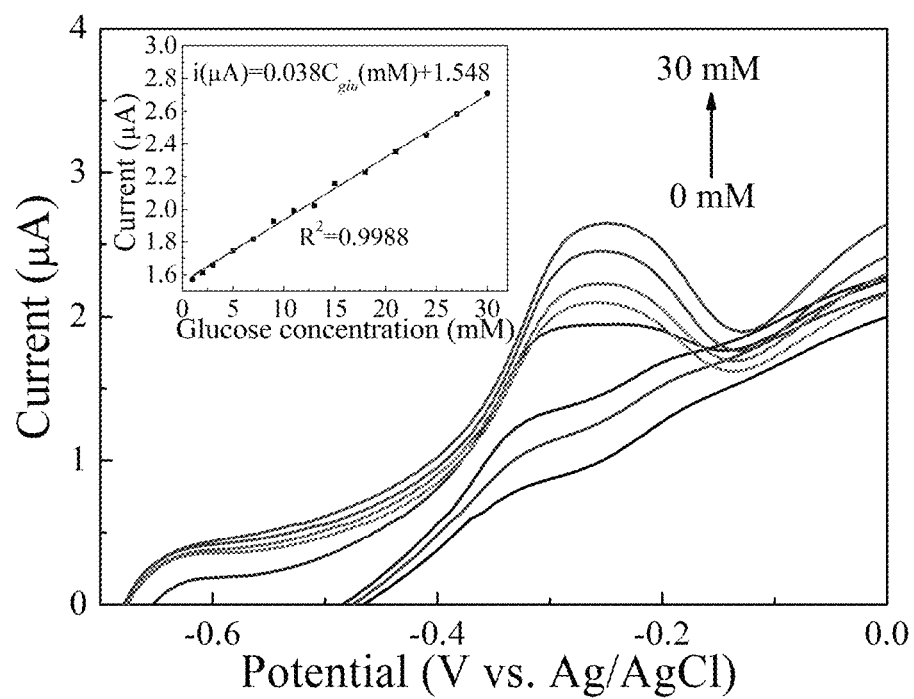
FIG. 8 is a cyclic voltammogram of the composite array electrode provided by the present invention for glucose detection.

Effectiveness Example 2—Detection of the Composite Array Electrode in Glucose Solutions of Different Concentrations The composite array electrode containing the nano platinum electrically conductive layer prepared by the preparation method of the present invention was placed in glucose solution of different concentrations for electrochemical detection to obtain a current-potential curve as shown in FIG. 8.

The results showed that the composite array electrode of the present invention exhibited a linear relationship for glucose having a concentration of 0-30 mM. Compared with the conventional electrode, the composite array electrode of the invention has a wider detection range for glucose. The linear relationship between the glucose concentration ($C_{glu}$) and the current (i) follows: $i(\mu A)=0.038\ C_{glu}(mM)+1.548$, correlation coefficient $R^2=0.9988$.

The foregoing descriptions are merely specific embodiments of the present invention, but are not intended to limit the protection scope of the present invention. Any variation or replacement readily figured out by a person skilled in the art within the technical scope disclosed in the present invention shall fall within the protection scope of the present invention. Therefore, the protection scope of the present invention shall be subject to the protection scope of the claims.

What is claimed is:

1. A composite array electrode comprising:
a microelectrode array substrate, and
a modification layer formed on a surface of a microelectrode of the microelectrode array substrate,
wherein the modification layer comprises a plurality of electrically conductive layers arranged at intervals on the surface of the microelectrode, an insulating layer arranged on the surface of the microelectrode except the electrically conductive layers, such that the plurality of electrically conductive layers are separated by the insulating layer, and wherein material for the electrically conductive layers comprises one or more of nano platinum, nano iridium, and carbon nanotubes.

2. The composite array electrode of claim 1, wherein each of the electrically conductive layers has a lateral dimension of 6 to 60 μm.

3. The composite array electrode of claim 1, wherein a plurality of the electrically conductive layers are arranged on the surface of the microelectrode in an array.

4. The composite array electrode of claim 1, wherein a total area of the electrically conductive layers is from 50% to 80% of the surface of the microelectrode.

5. The composite array electrode of claim 1, wherein the electrically conductive layers have a thickness of 0.02 to 10 μm.

6. The composite array electrode of claim 1, wherein an allowable difference between the thickness of the edge of the electrically conductive layers and the thickness of the central region of the electrically conductive layers is less than 0.1 μm.

7. The composite array electrode of claim 1, wherein cross-sectional shape of the electrically conductive layers comprises one or more of circle, triangle, quadrangle and polygon.

8. The composite array electrode of claim 1, wherein material for the insulating layer comprises, but is not limited to, one or more of polyimide, polydimethylsiloxane, polychloro-p-xylene, silica gel, polyurethane, silicone rubber and epoxy resin.

9. The composite array electrode of claim 1, wherein the carbon nanotubes are single-walled or multi-walled carbon nanotubes, and the carbon nanotubes have a pore size of 30 to 45 μm.

* * * * *